United States Patent
Kato

(10) Patent No.: US 10,925,473 B2
(45) Date of Patent: Feb. 23, 2021

(54) SOLID-STATE IMAGING DEVICE AND ENDOSCOPE SYSTEM

(71) Applicant: OLYMPUS CORPORATION, Hachioji (JP)

(72) Inventor: Hideki Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 28 days.

(21) Appl. No.: 16/525,880

(22) Filed: Jul. 30, 2019

(65) Prior Publication Data

US 2019/0350447 A1 Nov. 21, 2019

Related U.S. Application Data

(63) Continuation of application No. PCT/JP2017/010660, filed on Mar. 16, 2017.

(51) Int. Cl.
| | |
|---|---|
| *H04N 7/18* | (2006.01) |
| *A61B 1/045* | (2006.01) |
| *H04N 5/369* | (2011.01) |
| *H04N 5/378* | (2011.01) |

(52) U.S. Cl.
CPC .......... *A61B 1/045* (2013.01); *H04N 5/3698* (2013.01); *H04N 5/378* (2013.01)

(58) Field of Classification Search
CPC ...... H04N 5/3698; H04N 5/378; H04N 5/374; A61B 1/045; A61B 1/05
USPC ................... 348/76, 64, 65, 61, 68
See application file for complete search history.

(56) References Cited

U.S. PATENT DOCUMENTS

| | | | | |
|---|---|---|---|---|
| 9,667,892 | B2* | 5/2017 | Sakuragi | ................ H04N 5/378 |
| 2016/0005361 | A1* | 1/2016 | Kajiyama | ................ H04N 9/30 |
| | | | | 345/697 |
| 2017/0004770 | A1* | 1/2017 | Jin | ........................ H04N 13/398 |

FOREIGN PATENT DOCUMENTS

| | | |
|---|---|---|
| EP | 3 047 789 A1 | 7/2016 |
| JP | 2009-106343 A | 5/2009 |
| JP | 2016-214381 A | 12/2016 |
| WO | 2015/119070 A1 | 8/2015 |

OTHER PUBLICATIONS

International Search Report dated Jun. 6, 2017, issued in counterpart International Application No. PCT/JP2017/010660, w/English translation (2 pages).

* cited by examiner

*Primary Examiner* — Robert Chevalier

(74) *Attorney, Agent, or Firm* — Westerman, Hattori, Daniels & Adrian, LLP

(57) ABSTRACT

In a solid-state imaging device, a power supply voltage is input to a power supply terminal. A power supply line connects together the power supply terminal and a first control circuit. A detection circuit detects the power supply voltage input to the power supply terminal and a first digital signal corresponding to the detected power supply voltage. An output terminal outputs the first digital signal output from the detection circuit and a second digital signal corresponding to pixel signals.

13 Claims, 11 Drawing Sheets

SOLID-STATE IMAGING DEVICE AND ENDOSCOPE SYSTEM

The present application is a continuation application based on International Patent Application No. PCT/JP2017/010660 filed on Mar. 16, 2017, the content of which is incorporated herein by reference.

BACKGROUND OF THE INVENTION

Field of the Invention

The present invention relates to a solid-state imaging device and an endoscope system.

Description of Related Art

In a sensor system to which a power supply is connected with a long cable, the drop of a power supply voltage in the long cable cannot be ignored. Thus, a source of a power supply voltage needs to supply a high power voltage in anticipation of the voltage drop. The voltage drop varies according to the cable length, the sensor type, and the change in load current due to the environment.

In the technology disclosed in Japanese Unexamined Patent Application, First Publication No. 2009-106343, a monitoring unit is disposed in a scope in order to automatically adjust a power supply voltage according to the load state of the scope. A power supply circuit unit is disposed in a processor connected to the scope. The power supply circuit unit supplies the scope with a power supply voltage adjusted on the basis of a power supply voltage detected by the monitoring unit.

SUMMARY OF THE INVENTION

According to a first aspect of the present invention, a solid-state imaging device includes a plurality of pixels, a first control circuit, a power supply terminal, a power supply line, a detection circuit, and an output selecting circuit. The plurality of pixels are configured to generate pixel signals. The first control circuit is configured to control timings at which the pixel signals are read from the plurality of pixels. A power supply voltage is input to the power supply terminal. The power supply line connects together the power supply terminal and the first control circuit. The detection circuit is configured to detect the power supply voltage input to the power supply terminal after an imaging operation in the plurality of pixels is started, and output a first digital signal corresponding to the detected power supply voltage. The output selecting circuit is configured to selectively output the first digital signal output from the detection circuit and a second digital signal corresponding to the pixel signals to an output terminal.

According to a second aspect of the present invention, in the first aspect, the power supply voltage generated on the basis of the first digital signal output from the output terminal may be input to the power supply terminal.

According to a third aspect of the present invention, in the first aspect, the detection circuit may include a successive approximation register analog-to-digital converter (SAR-ADC).

According to a fourth aspect of the present invention, in the first aspect, the detection circuit may be configured to detect the power supply voltage at least once each time imaging of one frame is performed, and output the first digital signal.

According to a fifth aspect of the present invention, in the first aspect, the solid-state imaging device may further include an AD conversion circuit configured to generate the second digital signal corresponding to the pixel signals read from the plurality of pixels.

According to a sixth aspect of the present invention, in the fifth aspect, the solid-state imaging device may further include an output circuit configured to output the first digital signal output from the output selecting circuit in a first output period to the output terminal, and output the second digital signal output from the output selecting circuit in a second period different from the first output period to the output terminal.

According to a seventh aspect of the present invention, in the first aspect, the solid-state imaging device may further include an AD conversion circuit, an output circuit, and a second control circuit. The AD conversion circuit may be configured to generate the second digital signal corresponding to the pixel signals read from the plurality of pixels. The output circuit may be configured to output the second digital signal output from the output selecting circuit to the output terminal. The second control circuit may be configured to control the detection circuit such that the detection circuit outputs the first digital signal in a period during which the output circuit stops output of the second digital signal.

According to an eighth aspect of the present invention, in the seventh aspect, the first control circuit may be configured to control timings at which the plurality of pixels generate the pixel signals. The first control circuit may be configured to cause the plurality of pixels to generate the pixel signals in a first generation period, and thereafter cause the plurality of pixels to generate the pixel signals in a second generation period. The first control circuit may be configured to read the pixel signals generated in the first generation period from the plurality of pixels, and thereafter read the pixel signals generated in the second generation period from the plurality of pixels. The second control circuit may be configured to control the detection circuit such that the detection circuit outputs the first digital signal in a power supply signal output period. The power supply signal output period may be included in a period after the output circuit ends output of the second digital signal corresponding to the pixel signals generated in the first generation period. The power supply signal output period may be included in a period before the output circuit starts output of the second digital signal corresponding to the pixel signals generated in the second generation period.

According to a ninth aspect of the present invention, in the seventh aspect, the first control circuit may be configured to control timings at which the pixel signals are read from the plurality of pixels for each row in the arrangement of the plurality of pixels. The second control circuit may be configured to control the detection circuit such that the detection circuit detects the power supply voltage only in a reading period during which the pixel signals are read from the plurality of pixels. The reading period may not include a horizontal blanking period. The plurality of pixels may include the pixel in a first row and the pixel in a second row different from the first row. The horizontal blanking period may be included in a period after reading of the pixel signal from the pixel in the first row is ended. The horizontal blanking period may be included in a period before reading of the pixel signal from the pixel in the second row is started.

According to a tenth aspect of the present invention, in the ninth aspect, the plurality of pixels may include a plurality of optical black pixels. The second control circuit may be configured to control the detection circuit such that the detection circuit detects the power supply voltage only in a reading period of the pixel signals generated in the plurality of optical black pixels.

According to an eleventh aspect of the present invention, in the tenth aspect, the plurality of optical black pixels may include a first optical black pixel and a second optical black pixel. The second control circuit may be configured to control supply of the power supply voltage such that the power supply voltage is supplied to the detection circuit at a first timing. The first timing may be included in any one of a reading period of the pixel signal of the first optical black pixel and a period during which reading of all the pixel signals of the plurality of pixels is stopped. The second control circuit may be configured to control the detection circuit such that the detection circuit stops detection of the power supply voltage in a case where the first timing is included in the reading period of the pixel signal of the first optical black pixel. The second control circuit may be configured to control the detection circuit such that the detection circuit starts detection of the power supply voltage in a reading period of the pixel signal of the second optical black pixel. The reading period of the pixel signal of the second optical black pixel may be started at a second timing later than the first timing. The second control circuit may be configured to control supply of the power supply voltage such that supply of the power supply voltage to the detection circuit is stopped at a third timing later than the second timing.

According to a twelfth aspect of the present invention, in the first aspect, the detection circuit may be disposed within the solid-state imaging device.

According to a thirteenth aspect of the present invention, an endoscope system includes a circuit board and a control system. The circuit board includes the solid-state imaging device, a signal output circuit, and a power supply voltage input circuit. The signal output circuit is connected to the output terminal and is configured to output the first digital signal and the second digital signal output from the output terminal to the control system. The control system includes a signal input circuit, a power supply control circuit, a power supply voltage generation circuit, and a power supply voltage output circuit. The first digital signal and the second digital signal output from the signal output circuit are input to the signal input circuit. The power supply control circuit is configured to determine the power supply voltage on the basis of the first digital signal input to the signal input circuit. The power supply voltage generation circuit is configured to generate the power supply voltage determined by the power supply control circuit. The power supply voltage output circuit is configured to output the power supply voltage generated by the power supply voltage generation circuit to a power supply transmission line. The power supply voltage output to the power supply transmission line is input to the power supply voltage input circuit. The power supply voltage input to the power supply voltage input circuit is input to the power supply terminal.

DETAILED DESCRIPTION OF THE INVENTION

Embodiments of the present invention will be described with reference to the drawings. Each of the embodiments will be described in detail using an electronic endoscope system as an example of a sensor system to which a power supply is connected with a long cable.

First Embodiment

Figure 1:
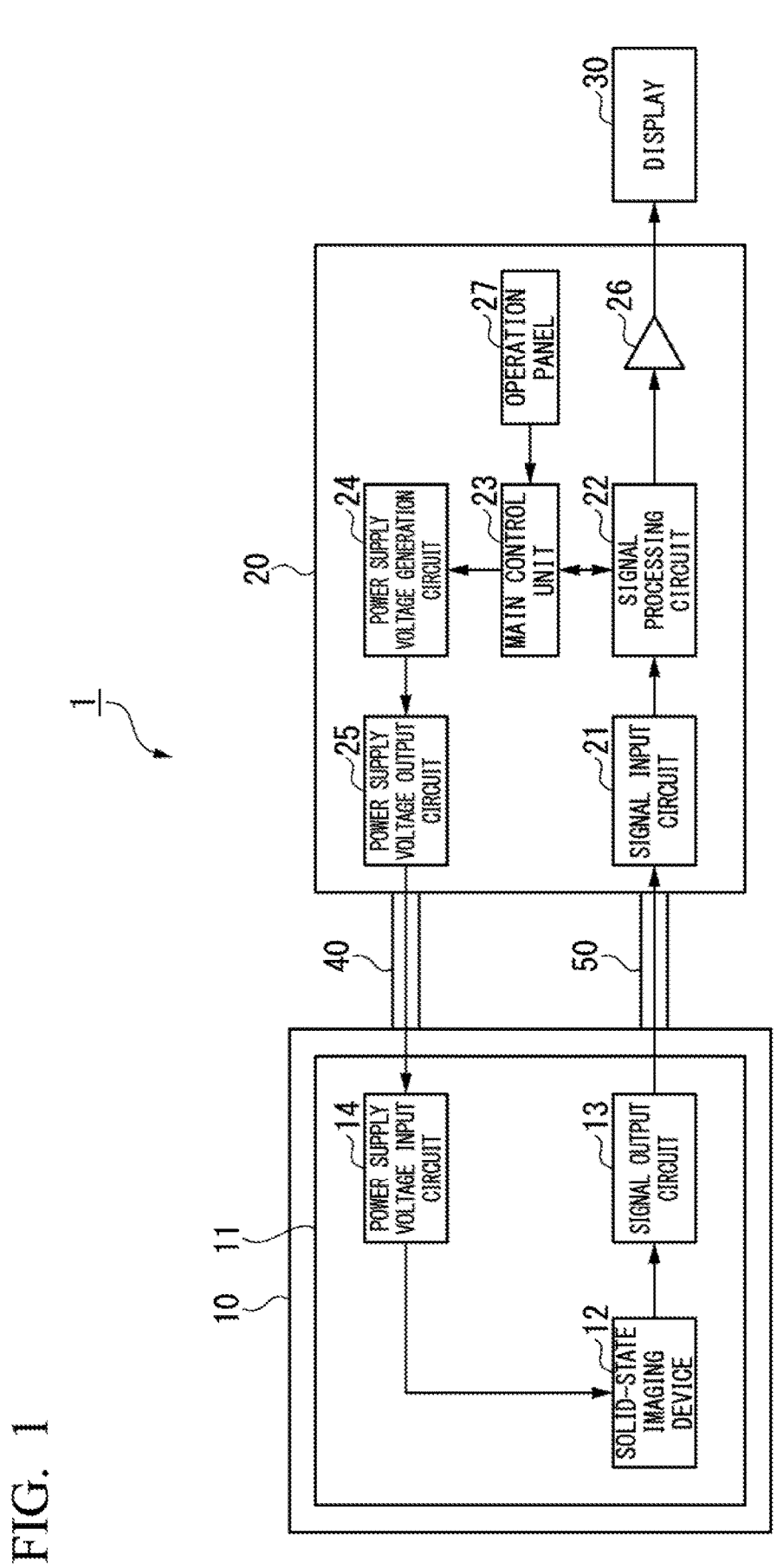
FIG. 1 is a block diagram showing a configuration of an electronic endoscope system according to a first embodiment of the present invention.

FIG. 1 shows a configuration of an electronic endoscope system 1 according to a first embodiment of the present invention. As shown in FIG. 1, the electronic endoscope system 1 includes a scope 10, a processor 20, a display 30, a power supply transmission line 40, and an image transmission line 50.

The scope 10 includes a circuit board 11. The circuit board 11 is disposed at the tip of the scope 10. The circuit board 11 includes a solid-state imaging device 12, a signal output circuit 13, and a power supply voltage input circuit 14. The processor 20 constitutes a control system. The processor 20 includes a signal input circuit 21, a signal processing circuit 22, a main control unit 23, a power supply voltage generation circuit 24, a power supply voltage output circuit 25, a signal output buffer 26, and an operation panel 27. The power supply transmission line 40 and the image transmission line 50 electrically connects together the scope 10 and the processor 20.

The solid-state imaging device 12 generates a pixel signal and outputs the generated pixel signal. Also, the solid-state imaging device 12 outputs a first digital signal representing a detected value of the power supply voltage. The pixel signal is output from the solid-state imaging device 12 as a second digital signal.

Figure 2:
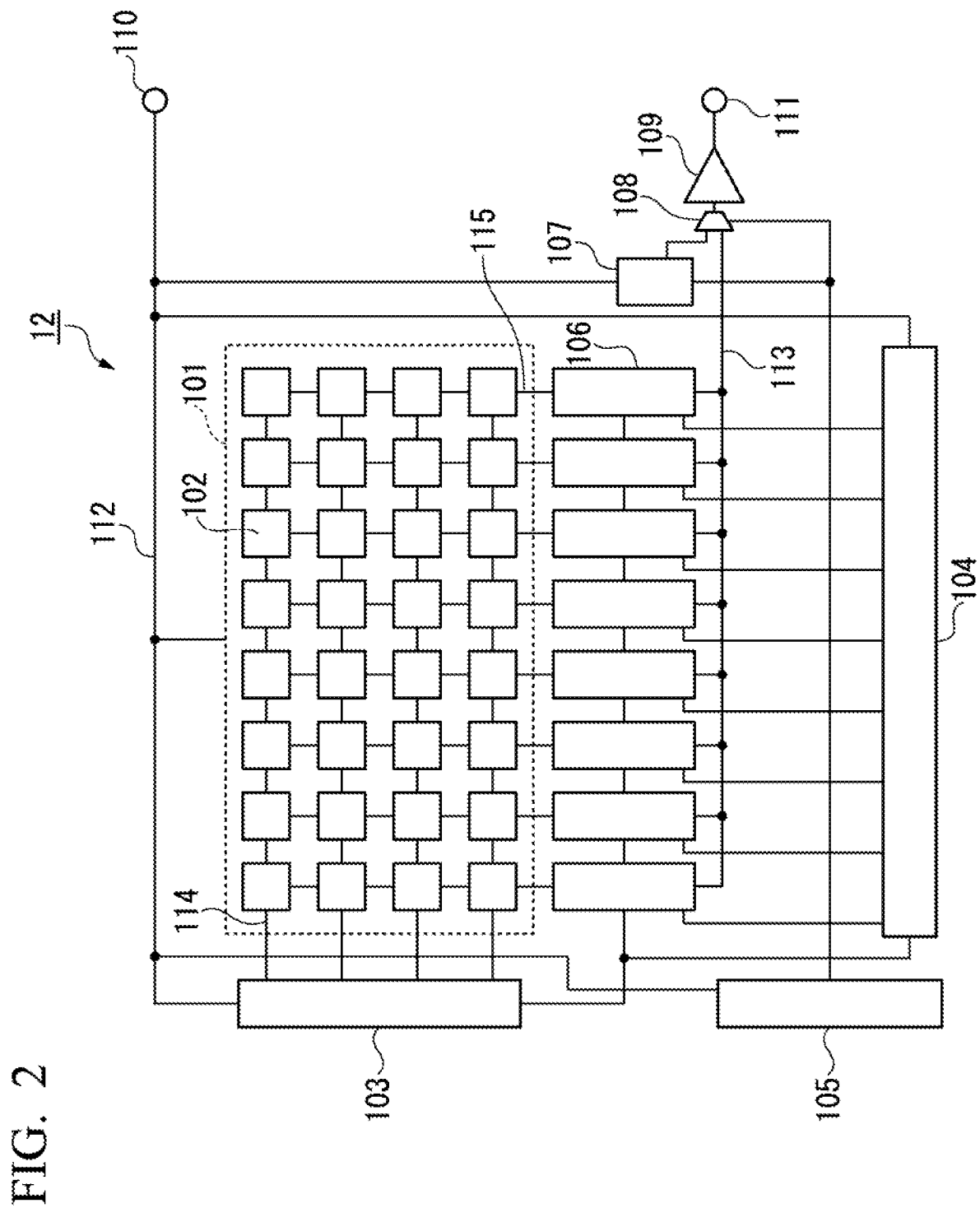
FIG. 2 is a block diagram showing a configuration of a solid-state imaging device according to the first embodiment of the present invention.

The signal output circuit 13 is connected to a signal output terminal 111 of the solid-state imaging device 12 (FIG. 2). The first and second digital signals output from the signal output terminal 111 are input to the signal output circuit 13. The signal output circuit 13 outputs the first and second digital signals to the processor 20. The first and second digital signals output from the signal output circuit 13 are input to the image transmission line 50 and transmitted to the processor 20 by the image transmission line 50. The signal output circuit 13 may be constituted as a signal output terminal.

The first and second digital signals output from the signal output circuit 13 are input to the signal input circuit 21. The signal input circuit 21 outputs the first and second digital signals to the signal processing circuit 22. The signal input circuit 21 may be constituted as a signal input terminal.

The signal processing circuit 22 distinguishes the first and second digital signals. The signal processing circuit 22 outputs a detected value based on the first digital signal to the main control unit 23. Also, the signal processing circuit 22 performs signal processing such as noise reduction, gamma correction, and demosaicing on the second digital signal. The signal processing circuit 22 outputs the second signal on which the signal processing has been performed to the signal output buffer 26.

The main control unit 23 (a power control circuit) performs various settings of the signal processing circuit 22. Also, the main control unit 23 determines a power supply voltage on the basis of the first digital signal input to the signal input circuit 21. That is, the main control unit 23 determines a power supply voltage on the basis of the detected value output from the signal processing circuit 22. The main control unit 23 stores the determined power supply voltage value and outputs the power supply voltage value to the power supply voltage generation circuit 24. Also, the main control unit 23 changes various settings of the electronic endoscope system 1 according to an instruction input to the operation panel 27 by a user.

The main control unit 23 may be constituted by at least one of a microprocessor and a logic circuit. For example, the logic circuit is at least one of an application specific integrated circuit (ASIC) and a field-programmable gate array (FPGA). The main control unit 23 can include one or a plurality of microprocessors. The main control unit 23 can include one or a plurality of logic circuits.

The power supply voltage generation circuit 24 generates a power supply voltage determined by the main control unit 23. That is, the power supply voltage generation circuit 24 generates a power supply voltage having the power supply voltage value output from the main control unit 23. The power supply voltage generation circuit 24 outputs the generated power supply voltage to the power supply voltage output circuit 25.

The power supply voltage output circuit 25 outputs the power supply voltage generated by the power supply voltage generation circuit 24 to the power supply transmission line 40. The power supply voltage output circuit 25 may be constituted as a signal output terminal. The power supply voltage output to the power supply transmission line 40 is transmitted to the scope 10.

The power supply voltage output to the power supply transmission line 40 is input to the power supply voltage input circuit 14. The power supply voltage input circuit 14 outputs the power supply voltage to the solid-state imaging device 12. The power supply voltage input circuit 14 may be constituted as a signal input terminal.

The signal output buffer 26 outputs the second digital signal output from the signal processing circuit 22 to the display 30. The operation panel 27 transmits an instruction from a user to the main control unit 23. The display 30 displays an image on the basis of the second digital signal output from the signal output buffer 26.

For example, the main control unit 23 determines the power supply voltage using the following method. Following Expression (1) shows a relationship between power supply voltages.

$$Vg1=Vd1+IR \quad (1)$$

Vg1 is a power supply voltage generated by the power supply voltage generation circuit 24. Vd1 is a power supply voltage detected in the solid-state imaging device 12. I represents current. R represents resistance in a transmission path of a power supply voltage. Therefore, IR represents voltage drop. Since the voltage drop IR occurs, the voltage Vd1 is lower than the correct operating voltage. The main control unit 23 calculates the voltage drop IR in Expression (1) on the basis of the voltage Vg1 and the voltage Vd1. Further, the main control unit 23 simply calculates a power supply voltage value using following Expression (2) based on Expression (1).

$$Vg2=Vd2+IR \quad (2)$$

Vg2 is a power supply voltage value output to the power supply voltage generation circuit 24. Vd2 is the correct operating voltage.

The method of determining a power supply voltage by the main control unit 23 is not limited to the above-mentioned method. The main control unit 23 may gradually increase a power supply voltage value until a power supply voltage detected in the solid-state imaging device 12 reaches the correct voltage.

In FIG. 1, an example in which a control system is constituted by an endoscope processor is shown. A control system may be constituted by an operation unit for operating an endoscope. Alternatively, a control system may be constituted by a combination of an operation unit and an endoscope processor.

FIG. 2 shows a configuration of the solid-state imaging device 12. An example in which the solid-state imaging device 12 is constituted by a complementary metal oxide semiconductor (CMOS) image sensor will be described. As shown in FIG. 2, the solid-state imaging device 12 includes a pixel array 101, a vertical scanning circuit 103, a horizontal scanning circuit 104, a timing generation circuit 105, a column circuit 106, a power supply voltage monitoring circuit 107, an output selecting circuit 108, a signal output circuit 109, a power supply terminal 110, and a signal output terminal 111. Also, the solid-state imaging device 12 includes a power supply line 112, a horizontal signal line 113, a row control line 114, and a vertical signal line 115.

The pixel array 101 includes a plurality of pixels 102 that are two-dimensionally arranged. Each of the plurality of pixels 102 includes a photoelectric conversion element and generates a pixel signal. The number of rows and columns in the arrangement of the plurality of pixels 102 is two or more.

The vertical scanning circuit 103 and the horizontal scanning circuit 104 constitute a first control circuit that controls timings at which pixel signals are read from the plurality of pixels 102. The vertical scanning circuit 103 controls timings at which pixel signals are read from the plurality of pixels 102 for each row in the arrangement of the plurality of pixels 102. The vertical scanning circuit 103 outputs a control signal to the row control line 114 connected to the pixels 102 in each row. By doing this, the vertical scanning circuit 103 controls output of pixel signals from the 102 in each row to the vertical signal line 115. The vertical signal line 115 is connected to the pixels 102 in each column.

A plurality of column circuits 106 are disposed. The column circuit 106 is connected to the vertical signal line 115 corresponding to the pixels 102 in each column. The column circuit 106 performs signal processing such as noise reduction, signal amplification, and analog-to-digital conversion (AD conversion) on the pixel signals output from the pixels 102 to the vertical signal line 115. Therefore, the column circuit 106 constitutes an AD conversion circuit that generates the second digital signal corresponding to the pixel signals read from the plurality of pixels 102.

The horizontal scanning circuit 104 performs control of sequentially transferring a plurality of pixel signals read from the pixels 102 in a plurality of columns to the output selecting circuit 108. The horizontal scanning circuit 104 causes the plurality of column circuits 106 to sequentially output the second digital signal to the horizontal signal line 113. The horizontal signal line 113 is connected to the column circuits 106 and the output selecting circuit 108. The second digital signal sequentially output from the plurality of column circuits 106 to the horizontal signal line 113 is transferred to the output selecting circuit 108 by the horizontal signal line 113.

A power supply voltage input to the power supply voltage input circuit 14 is input to the power supply terminal 110. The power supply line 112 is connected to the power supply terminal 110. Further, the power supply line 112 is connected to the pixel array 101, the vertical scanning circuit 103, the horizontal scanning circuit 104, the timing generation circuit 105, the power supply voltage monitoring circuit 107, and the like. Therefore, the power supply line 112 connects together the power supply terminal 110 and the above-mentioned circuits. The above-mentioned circuits operate with the power supply voltage input to the power supply terminal 110.

The power supply voltage monitoring circuit 107 (a detection circuit) detects the power supply voltage input to the power supply terminal 110 after an imaging operation is started in the plurality of pixels 102, and outputs the first digital signal corresponding to the detected power supply voltage. The first digital signal output from the power supply voltage monitoring circuit 107 is input to the output selecting circuit 108.

The output selecting circuit 108 and the signal output circuit 109 constitute an output circuit that output the first and second digital signals to the signal output terminal 111. The output selecting circuit 108 selects any one of the first signal and the second digital signal and outputs the selected signal to the signal output circuit 109. The output selecting circuit 108 switches the selected signal between the first signal and the second digital signal. The signal output circuit 109 converts the form of the first and second digital signals output from the output selecting circuit 108 to the form suitable for high-speed signal transmission. The signal output circuit 109 outputs the first and second digital signals having the form suitable for high-speed signal transmission to the signal output terminal 111.

The signal output terminal 111 is connected to the signal output circuit 109. The signal output terminal 111 outputs the first and second digital signals output from the signal output circuit 109 to an external circuit, that is, the signal output circuit 13.

The timing generation circuit 105 controls operation timings of the scanning circuit 103, the horizontal scanning circuit 104, the column circuit 106, the power supply voltage monitoring circuit 107, and the output selecting circuit 108. The timing generation circuit 105 constitutes a second control circuits that controls the power supply voltage monitoring circuit 107. Also, the timing generation circuit 105 controls timings at which the first and second digital signals are output from the output selecting circuit 108 by controlling the output selecting circuit 108.

The first digital signal output from the signal output terminal 111 is transmitted to the processor 20 by the image transmission line 50. The power supply voltage generated on the basis of the first digital signal by the power supply voltage generation circuit 24 in the processor 20 is input to the power supply terminal 110.

The signal output terminal 111 may be constituted by a first output terminal and a second output terminal different from the first output terminal. The first output terminal outputs the first digital signal. The second output terminal outputs the second digital signal. In the example shown in FIG. 2, the first output terminal and the second output are the same.

The signal output circuit 13 may be constituted by a first output circuit and a second output circuit. The first output circuit is connected to the first output terminal and outputs the first digital signal output from the first output terminal to the processor 20. The second output circuit is connected to the second output terminal and outputs the second digital signal output from the second output terminal to the processor 20.

The signal input circuit 21 may be constituted by a first input circuit and a second input circuit. The first digital signal output from the first signal output circuit is input to the first input circuit. The second digital signal output from the second signal output circuit is input to the second input circuit.

Analog pixel signals may be output from the solid-state imaging device 12. Therefore, the signal output terminal 111 may output the pixel signals read from the plurality of pixels 102. The signal output circuit 13 may output the pixel signals output from the signal output terminal 111 to the processor 20. The pixel signals output from the signal output circuit 13 may be input to the signal input circuit 21.

Figure 3:
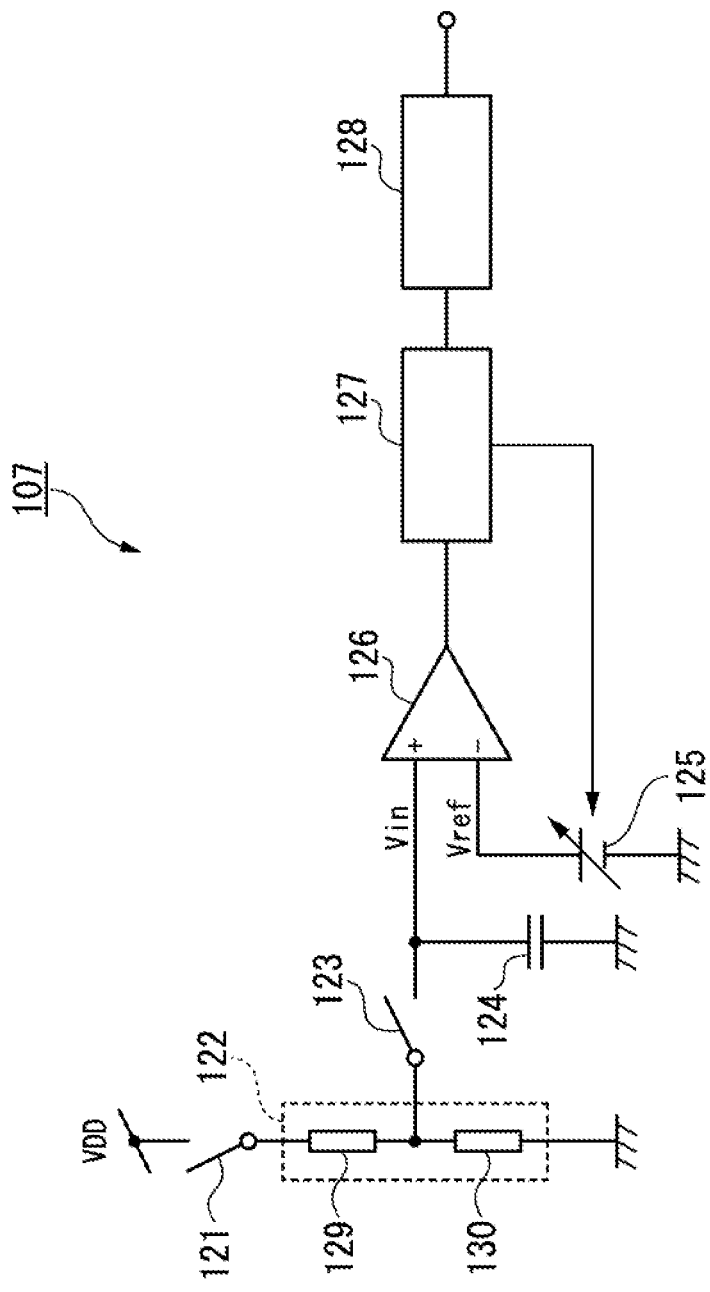
FIG. 3 is a circuit diagram showing a configuration of a power supply voltage monitoring circuit according to the first embodiment of the present invention.

For example, the power supply voltage monitoring circuit 107 is constituted by a successive approximation register analog-to-digital converter (SAR-ADC). FIG. 3 shows a configuration of the power supply voltage monitoring circuit 107 constituted by the SAR-ADC. As shown in FIG. 3, the power supply voltage monitoring circuit 107 includes a detection switch 121, an attenuator 122, a sample-and-hold (SH) switch 123, an SH capacitor 124, a reference voltage generation circuit 125, a comparator 126, a successive approximation logic 127, and a latch circuit 128.

The detection switch 121 includes a first terminal and a second terminal. A power supply voltage VDD is input to the first terminal of the detection switch 121. The second terminal of the detection switch 121 is connected to the attenuator 122. The state of the detection switch 121 is switched between on and off. When the detection switch 121 is on, the first and second terminals of the detection switch 121 are electrically connected to each other. At this time, the power supply voltage VDD is input to the attenuator 122. When the detection switch 121 is off, the first and second terminals of the detection switch 121 are in a high impedance state. The state of the detection switch 121 is controlled by the timing generation circuit 105.

The attenuator 122 includes a first resistor 129 and a second resistor 130 that are attenuation resistors. Each of the first resistor 129 and the second resistor 130 includes a first terminal and a second terminal. The first terminal of the first resistor 129 is connected to the second terminal of the detection switch 121. The first terminal of the second resistor 130 is connected to the second terminal of the first resistor 129. The second terminal of the second resistor 130 is connected to the ground. The attenuator 122 attenuates the power supply voltage VDD with an amplification factor (an attenuation factor) a according to a ratio of resistance values of the first resistor 129 and the second resistor 130. The attenuator 122 outputs an attenuated power supply voltage Vin. The value of the power supply voltage Vin is a times the value of the power supply voltage VDD. When the resistance value of the first resistor 129 is Ra and the resistance value of the second resistor 130 is Rb, the amplification factor α is represented by following Expression (1).

$$\alpha = Rb/(Ra+Rb) \qquad (1)$$

The SH switch 123 includes a first terminal and a second terminal. The first terminal of the SH switch 123 is connected to the second terminal of the first resistor 129 and the first terminal of the second resistor 130. The second terminal of the SH switch 123 is connected to the SH capacitor 124 and the comparator 126. The state of the SH switch 123 is switched between on and off. When the SH switch 123 is on, the first and second terminals of the SH switch 123 are electrically connected to each other. At this time, the power supply voltage Vii is input to the SH capacitor 124. When the SH switch 123 is off, the first and second terminals of the SH switch 123 are in a high impedance state. The state of the SH switch 123 is controlled by the timing generation circuit 105. The SH switch 123 samples the power supply voltage Vi.

The SH capacitor 124 includes a first terminal and a second terminal. The first terminal of the SH capacitor 124 is connected to the second terminal of the SH switch 123. The second terminal of the SH capacitor 124 is connected to the ground. The SH capacitor 124 holds the power supply voltage Vin sampled by the SH switch 123.

The reference voltage generation circuit 125 is a variable voltage source. The reference voltage generation circuit 125 is constituted by a digital-to-analog (DA) conversion circuit. The reference voltage generation circuit 125 generates a reference voltage Vref. The reference voltage Vref generated by the reference voltage generation circuit 125 is output to the comparator 126.

The comparator 126 includes a non-inverted input terminal (+), an inverted input terminal (−), and an output terminal. The non-inverted input terminal of the comparator 126 is connected to the second terminal of the SH switch 123 and the first terminal of the SH capacitor 124. The inverted input terminal of the comparator 126 is connected to the reference voltage generation circuit 125. The power supply voltage Vin is input to the non-inverted input terminal of the comparator 126 and the reference voltage Vref is input to the inverted input terminal of the comparator 126. The comparator 126 compares the power supply voltage Vin with the reference voltage Vref and outputs comparison results to the successive approximation logic 127 through the output terminal. The comparator 126 performs comparison for each bit of the first digital signal that represents results of AD conversion.

The successive approximation logic 127 outputs a digital signal according to the comparison results output from the comparator 126 to the reference voltage generation circuit 125. The reference voltage generation circuit 125 outputs the reference voltage Vref corresponding to the digital signal output from the successive approximation logic 127 to the comparator 126. The successive approximation logic 127 outputs the comparison results output from the comparator 126 to the latch circuit 128.

The latch circuit 128 holds the comparison results. After the comparison results of all the bits of the first digital signal are determined, the latch circuit 128 outputs the first digital signal based on the comparison results.

Figure 4:
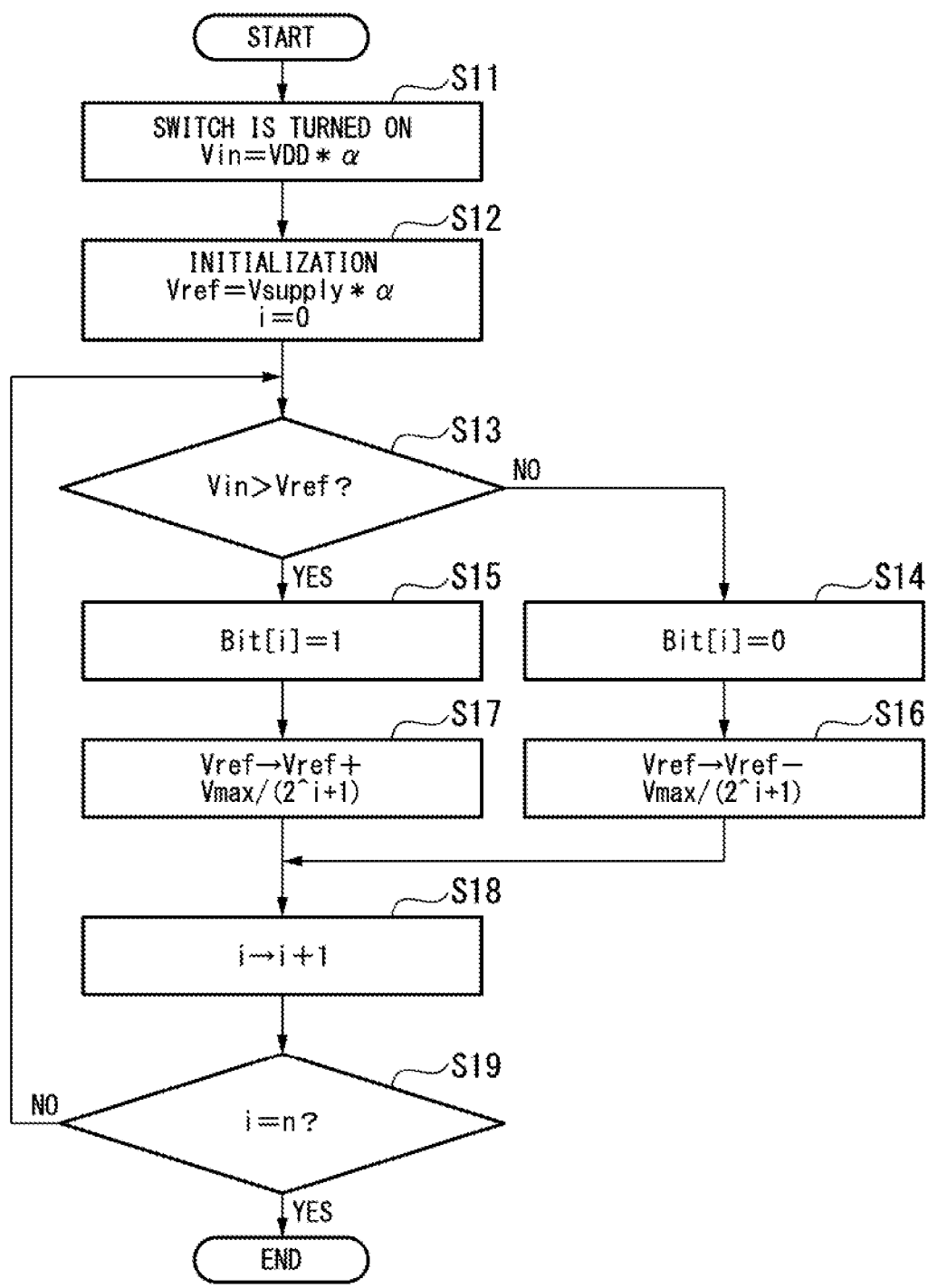
FIG. 4 is a flow chart showing a sequence of power supply voltage detection using the power supply voltage monitoring circuit according to the first embodiment of the present invention.

FIG. 4 shows a sequence of power supply voltage detection using the power supply voltage monitoring circuit 107. The number of bits of digital data constituting the first digital data output from the power supply voltage monitoring circuit 107 is n. A code of the digital data is sequentially determined bit by bit. A detection bit i represents a bit in conversion.

In step S11, when the detection switch 121 and the SH switch 123 are turned on, the power supply voltage Vin is input to the SH capacitor 124. Thereafter, the SH switch 123 is turned off, and thus the power supply voltage Vin is held in the SH capacitor 124.

In step S12, the successive approximation logic 127 is initialized. Thus, the reference voltage Vref becomes Vsupply*α. Vsupply is a predetermined voltage. At this time, the detection bit i is set to 0.

In step S13, the comparator 126 compares the power supply voltage Vin with the reference voltage Vref. When the power supply voltage Vin is higher than the reference voltage Vref, Bit[i] is set to 1 (step S15). Bit[i] of the first digital signal is the i-th bit. When the power supply voltage Vin is lower than the reference voltage Vref Bit[i] is set to 0 (step S14).

The comparison results are held in the successive approximation logic 127. The successive approximation logic 127 outputs a digital signal based on the held comparison results to the reference voltage generation circuit 125. The reference voltage generation circuit 125 changes the reference voltage Vref on the basis of the digital signal. In a case where Bit[i] is 1, the changed reference voltage Vref is S represented in Expression (2) (step S17). In a case where Bit[i] is 0, the changed reference voltage Vref is represented in Expression (3) (step S16).

$$V\text{ref}' = V\text{ref} + V\text{max}/(2^i+1) \qquad (2)$$

$$V\text{ref}' = V\text{ref} - V\text{max}/(2^i+1) \qquad (3)$$

The reference voltage Vref is changed, and thus conversion of the i-th bit is complete. In step S18, 1 is added to i. In step S19, when i is not equal to n, conversion of the next bit is started. At this time, processes starting in step S13 are similarly executed. In step S19, when i is equal to n, power supply voltage detection ends.

After power supply voltage detection is started, the detection switch 121 is kept in a state of on. After power supply voltage detection ends, the detection switch 121 is turned off. Thus, supply of the power supply voltage to the successive approximation logic 127 is stopped.

Figure 5:
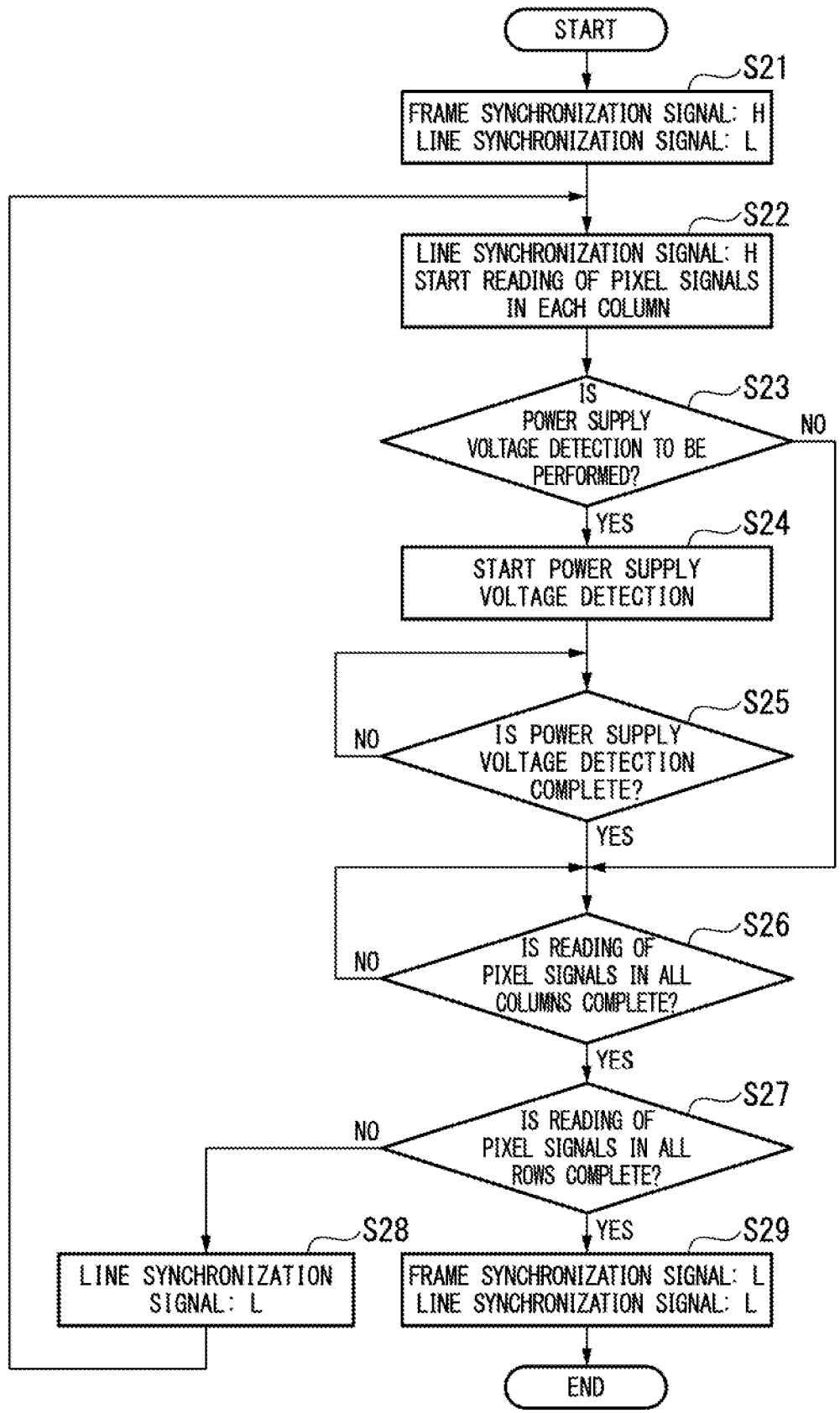
FIG. 5 is a flow chart showing a sequence of pixel signal reading and power supply voltage detection in the first embodiment of the present invention.

FIG. 5 shows a sequence of pixel signal reading and power supply voltage detection. A frame synchronization signal and a line synchronization signal are supplied from a drive circuit not shown in FIG. 1 to the solid-state imaging device 12.

After an imaging operation in the solid-state imaging device 12 is started, the frame synchronization signal is switched from L (a low level) to H (a high level) in step S21. Thus, pixel signal reading is sequentially started from the pixels 102 in the first row. At this time, the line synchronization signal is in L.

Specifically, pixel signals based on electric charges generated through photoelectric conversion in the pixels 102 in each row are read to the vertical signal line 115. Pixel signal reading in the pixels 102 is controlled by the vertical scanning circuit 103. While the line synchronization signal is in L, the pixel signals of the pixels 102 in each of the columns in the same row are read. The pixel signal is converted into the second digital signal by the column circuit 106. The second digital signal is held in a memory mounted in the column circuit 106.

In step S22, the line synchronization signal is switched from L to H. Thus, reading of the second digital signal held in the column circuit 106 is started. In reading of the second digital signal, the second digital signal is read to the horizontal signal line 113 for each column. Reading of the second digital signal in the column circuit 106 is controlled by the horizontal scanning circuit 104.

When reading of the second digital signal is started, it is determined whether or not to perform power supply voltage detection in step S23. Determination in step S23 is repeated until a predetermined condition is satisfied. When the predetermined condition is satisfied and thus it is determined to perform power supply voltage detection, power supply voltage detection is started in step S24. Power supply voltage detection is performed in accordance with the sequence shown in FIG. 4.

After power supply voltage detection is started, it is determined whether or not power supply voltage detection is complete in step S25. When power supply voltage detection is not complete, determination in step S25 is repeated until power supply voltage detection is complete. In parallel with power supply voltage detection, reading of pixel signals in each column is performed.

When it is determined that power supply voltage detection is complete, it is determined whether or not reading of pixel signals of the pixels 102 in all the columns in the same row is complete in step S26. Also, when it is determined not to perform power supply voltage detection in step S23, determination in step S26 is performed without performing power supply voltage detection. When there is a column in which the pixel signal is not read, determination in step S26 is repeated.

When it is determined that reading of pixel signals of the pixels 102 in all the columns in the same row is complete, it is determined whether or not reading of pixel signals of the pixels 102 in all the rows is complete in step S27. When there is a row in which the pixel signal is not read, the line synchronization signal is switched from H to L in step S28. Thereafter, reading of pixel signals of the pixels 102 in the next row is started.

When it is determined that reading of pixel signals of the pixels 102 in all the rows is complete, the frame synchronization signal is switched from H to L and the line synchronization signal is switched from H to L in step S29. Thus, reading of pixel signals of one frame is complete.

Determination in step S23 is performed on the basis of a timing stored in advance in the timing generation circuit 105. For example, the power supply voltage monitoring circuit 107 performs power supply voltage detection at a timing at which reading of pixel signals of optical black (OB) pixels is performed.

In the operation shown in FIG. 5, the timing generation circuit 105 controls the power supply voltage monitoring circuit 107 such that the power supply voltage monitoring circuit 107 detects the power supply voltage only in a reading period of pixel signals generated in the plurality of pixels 102. In the reading period of pixel signals, the line synchronization signal is in H. The timing generation circuit 105 may control the power supply voltage monitoring circuit 107 such that the power supply voltage monitoring circuit 107 detects the power supply voltage in a period during which reading of pixel signals is stopped.

Figure 6:
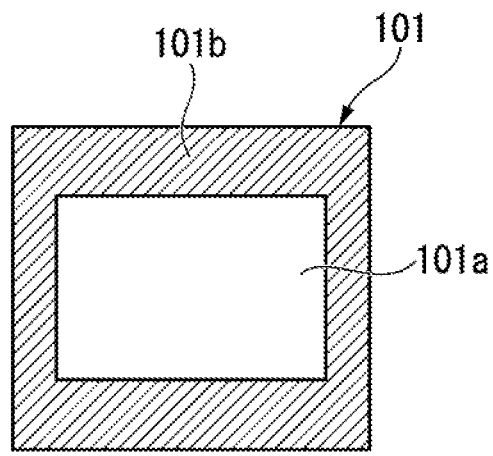
FIG. 6 is a reference diagram showing a pixel array according to the first embodiment of the present invention.

FIG. 6 shows the pixel array 101. In FIG. 6, an example in which the pixel array 101 contains two regions is shown. The pixel array 101 contains an effective pixel region 101a and an OB pixel region 101b. The effective pixel region 101a is a region that includes the pixels 102 in which light irradiated to the solid-state imaging device 12 is incident and pixel signals based on the light are generated. The OB pixel region 101b is a region that includes a structure for blocking light irradiated to the solid-state imaging device 12 such that the light is not incident in the pixels 102. For example, a wiring layer constitutes the structure for blocking light.

The effective pixel region 101a includes the pixels 102 in a plurality of rows and columns disposed at the center of the pixel array 101. The OB pixel region 101b includes the pixels 102 in a plurality of rows and columns around the effective pixel region 101a. That is, the OB pixel region 101b includes OB pixels. The pixel signals read from the OB pixels are used for correcting a dark current component and a variation between column circuits 106. The OB pixels are shielded from light, and thus the level of signals output from the OB pixels is almost constant. For this reason, it is possible to suppress the fluctuation of current consumption according to signal levels. Consequently, noise mixed in the power supply voltage when the power supply voltage monitoring circuit 107 performs power supply voltage detection is reduced.

Figure 7:
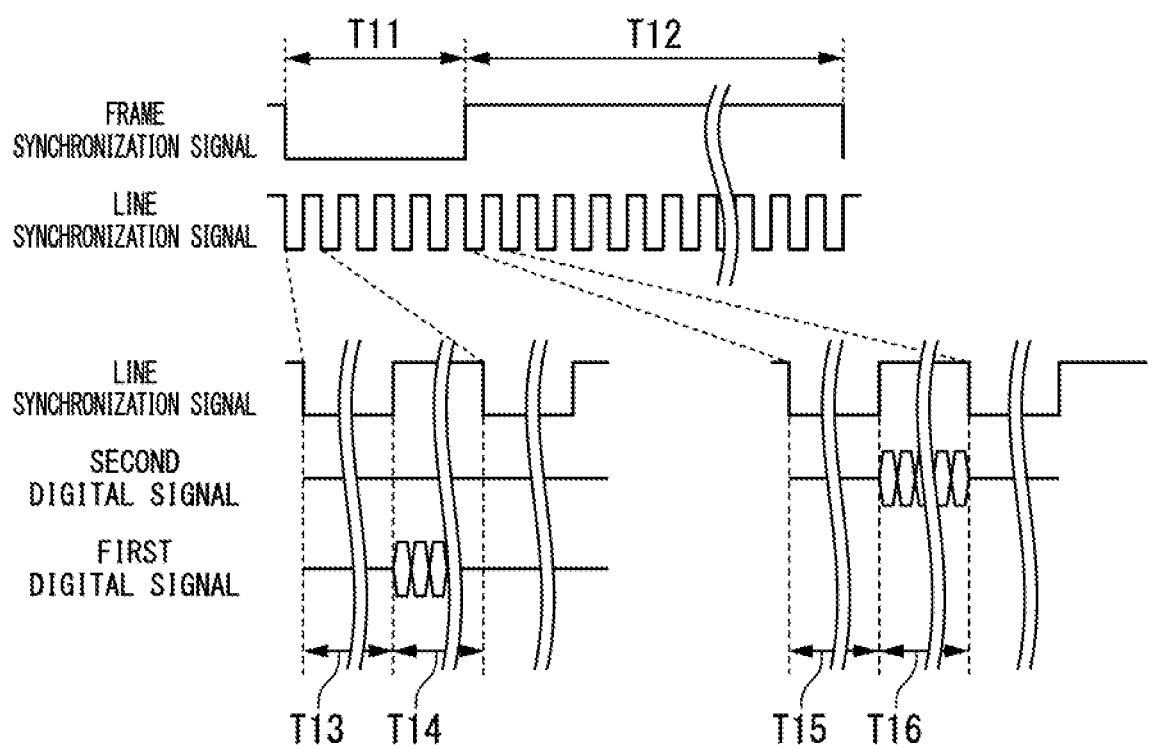
FIG. 7 is a timing chart showing signals regarding an operation of the solid-state imaging device according to the first embodiment of the present invention.
Figure 8:
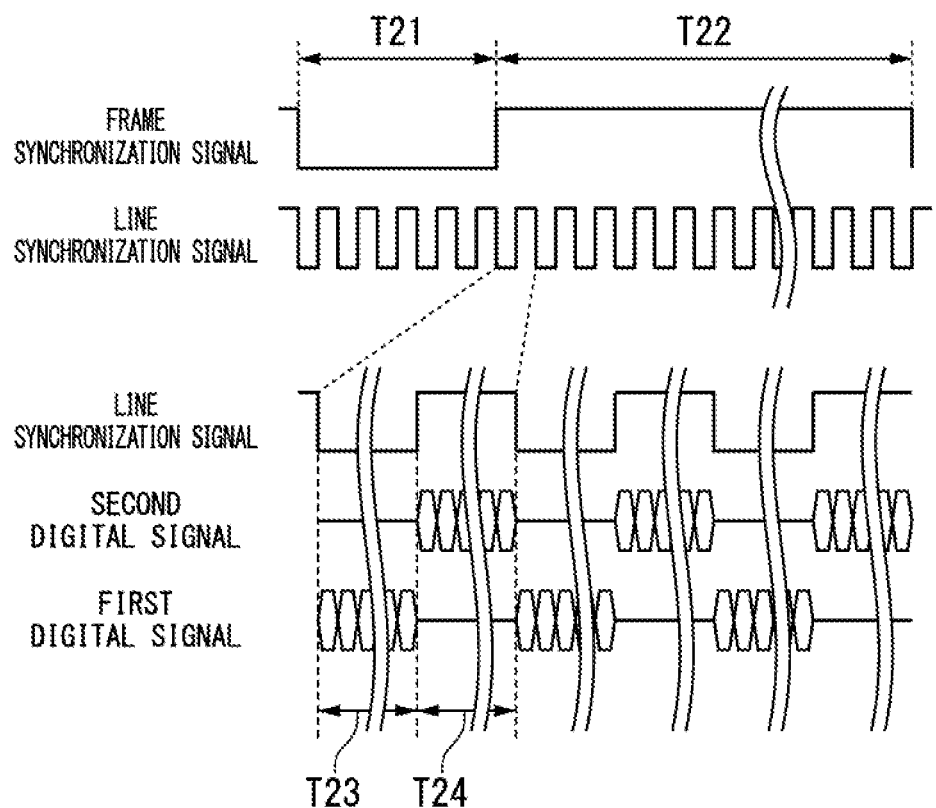
FIG. 8 is a timing chart showing signals regarding an operation of the solid-state imaging device according to the first embodiment of the present invention.

FIGS. 7 and 8 show signals regarding an operation of the solid-state imaging device 12. In FIGS. 7 and 8, waveforms of the frame synchronization signal, the line synchronization signal, the second digital signal, and the first digital signal are shown. In FIGS. 7 and 8, the horizontal direction represents time and the vertical direction represents a voltage. In FIGS. 7 and 8, waveforms of the signals in one frame are shown. In a plurality of frames, the operation shown in FIGS. 7 and 8 is repeated.

An output period of the first and second digital signals will be described with reference to FIG. 7. A period T11 during which the frame synchronization signal is in L is a blanking period. In the blanking period, the output selecting circuit 108 and the signal output circuit 109 stop output of the second digital signal corresponding to the pixel signals. In a period T14 during which the line synchronization signal is in H in the blanking period, the output selecting circuit 108 and the signal output circuit 109 output the first digital signal representing detection results of the power supply voltage.

A period T12 during which the frame synchronization signal is in H is a frame output period. A period T16 during which the line synchronization signal is in H in the frame output period is a horizontal reading period. In the horizontal reading period, the output selecting circuit 108 and the signal output circuit 109 output the second digital signal. In the horizontal reading period, the power supply voltage monitoring circuit 107 detects the power supply voltage. In the blanking period or a horizontal blanking period, the power supply voltage monitoring circuit 107 may detect the power supply voltage. The power supply voltage monitoring circuit 107 detects the power supply voltage at least once each time imaging of one frame is performed, and outputs the first digital signal.

A period T13 and a period T15 during which the line synchronization signal is in L are the horizontal blanking period. In the horizontal blanking period, the output selecting circuit 108 and the signal output circuit 109 stop output of the first and second digital signals.

The output selecting circuit 108 and the signal output circuit 109 output the first digital signal to the signal output terminal 111 in a first output period (the period T14). For example, the output selecting circuit 108 and the signal output circuit 109 output the first digital signal corresponding to the power supply voltage detected in a first frame to the signal output terminal 111 in the first output period of a second frame following the first frame. The output selecting circuit 108 and the signal output circuit 109 output the second digital signal to the signal output terminal 111 in a second output period (the period T16) different from the first output period.

The timing generation circuit 105 controls the power supply voltage monitoring circuit 107 such that the power supply voltage monitoring circuit 107 outputs the first digital signal in the period T14 during which the output selecting circuit 108 and the signal output circuit 109 stop output of the second digital signal. In other words, the timing generation circuit 105 causes the power supply voltage monitoring circuit 107 to output the first digital signal in the period T14. The timing generation circuit 105 also controls the output selecting circuit 108 such that the output selecting circuit 108 outputs the first digital signal in the period T14.

The vertical scanning circuit 103 controls timings at which the plurality of pixels 102 generate pixel signals. The vertical scanning circuit 103 causes the plurality of pixels 102 to generate pixel signals in a first generation period, and thereafter causes the plurality of pixels 102 to generate pixel signals in a second generation period. The first generation period is the frame output period (the period T12) in the first frame. The second generation period is the frame output period in the second frame following the first frame. The vertical scanning circuit 103 reads the pixel signals generated in the first generation period from the plurality of pixels 102, and thereafter reads the pixel signals generated in the second generation period from the plurality of pixels 102.

The timing generation circuit 105 controls the power supply voltage monitoring circuit 107 such that the power supply voltage monitoring circuit 107 outputs the first digital signal in a power supply signal output period (the period T14). The power supply signal output period is included in a period after the output selecting circuit 108 and the signal output circuit 109 end output of the second digital signal corresponding to the pixel signals generated in the first generation period. Also, the power supply signal output period is included in a period before the output selecting circuit 108 and the signal output circuit 109 starts output of the second digital signal corresponding to the pixel signals generated in the second generation period.

In other words, the timing generation circuit 105 causes the power supply voltage monitoring circuit 107 to output the first digital signal in the power supply signal output period. The timing generation circuit 105 also controls the output selecting circuit 108 such that the output selecting circuit 108 outputs the first digital signal in the power supply signal output period.

An output period of the first and second digital signals will be described with reference to FIG. 8. A period T21 during which the frame synchronization signal is in L is a blanking period. In the blanking period, the output selecting circuit 108 and the signal output circuit 109 stop output of the first and second digital signals. A period T22 during which the frame synchronization signal is in H is a frame output period. In the frame output period, the output selecting circuit 108 and the signal output circuit 109 output the first and second digital signals.

A period T23 during which the line synchronization signal is in L in the frame output period is a horizontal blanking period. In the horizontal blanking period, the output selecting circuit 108 and the signal output circuit 109 stop output of the second digital signal. Also, in the horizontal blanking period, the output selecting circuit 108 and the signal output circuit 109 output the first digital signal.

A period T24 during which the line synchronization signal is in H in the frame output period is a horizontal reading period. In the horizontal reading period, the output selecting circuit 108 and the signal output circuit 109 output the second digital signal. Also, in the horizontal reading period, the output selecting circuit 108 and the signal output circuit 109 stop output of the first digital signal. In the horizontal reading period, the power supply voltage monitoring circuit 107 detects the power supply voltage. In the blanking period or the horizontal blanking period, the power supply voltage monitoring circuit 107 may detect the power supply voltage. The power supply voltage monitoring circuit 107 detects the power supply voltage at least once each time imaging of one frame is performed, and outputs the first digital signal.

The output selecting circuit 108 and the signal output circuit 109 output the first digital signal to the signal output terminal 111 in a first output period (the period T23). The output selecting circuit 108 and the signal output circuit 109 output the second digital signal to the signal output terminal 111 in a second output period (the period T24) different from the first output period.

The timing generation circuit 105 controls the power supply voltage monitoring circuit 107 such that the power supply voltage monitoring circuit 107 outputs the first digital signal in the period T23 during which the output selecting circuit 108 and the signal output circuit 109 stop output of the second digital signal. In other words, the timing generation circuit 105 causes the power supply voltage monitoring circuit 107 to output the first digital signal in the period T23. The timing generation circuit 105 also controls the output selecting circuit 108 such that the output selecting circuit 108 outputs the first digital signal in the period T23.

The timing generation circuit 105 controls the power supply voltage monitoring circuit 107 such that the power supply voltage monitoring circuit 107 detects the power supply voltage only in a reading period (the period T24) during which pixel signals are read from the plurality of pixels 102. This reading period does not include the horizontal blanking period (the period T23). The horizontal blanking period is included in a period after reading of pixel signals from the pixels 102 in a first row is ended. The horizontal blanking period is included in a period before reading of pixel signals from the pixels 102 in a second row different from the first row is started.

The timing generation circuit 105 controls the output selecting circuit 108 and the signal output circuit 109 such that the output selecting circuit 108 and the signal output circuit 109 alternately output the first digital signal and the second digital signal. In other words, the timing generation circuit 105 causes the output selecting circuit 108 and the signal output circuit 109 to alternately output the first digital signal and the second digital signal.

The timing generation circuit 105 controls the power supply voltage monitoring circuit 107, the output selecting circuit 108, and the signal output circuit 109 such that the power supply voltage monitoring circuit 107 detects the power supply voltage and at the same time the output selecting circuit 108 and the signal output circuit 109 output the second signal.

The plurality of pixels 102 include a plurality of OB pixels. The timing generation circuit 105 may control the power supply voltage monitoring circuit 107 such that the power supply voltage monitoring circuit 107 detects the power supply voltage only in a reading period (the period T24) of pixel signals generated in the plurality of OB pixels. In other words, the timing generation circuit 105 may cause the power supply voltage monitoring circuit 107 to detect the power supply voltage only in a reading period of pixel signals generated in the plurality of OB pixels.

The plurality of OB pixels may include a first OB pixel and a second OB pixel. For example, the second OB pixel is the pixel 102 that is disposed in a row in which the first OB pixel is disposed and in a column different from a column in which the first OB pixel is disposed.

The timing generation circuit 105 controls supply of the power supply voltage such that the power supply voltage is supplied to the power supply voltage monitoring circuit 107 at a first timing. The first timing is a timing of step S11 in FIG. 4. The timing generation circuit 105 controls the detection switch 121 and the SH switch 123 such that the power supply voltage Vin is held in the SH capacitor 124.

The first timing is included in any one of a reading period of pixel signals of the first OB pixels and a period during which reading of all pixel signals of the plurality of pixels 102 is stopped. The reading period of pixel signals of the first OB pixels is the period T16 and the period T24, namely the horizontal reading period. The period during which reading of all pixel signals of the plurality of pixels 102 is stopped is the period T11 and the period T21, namely the blanking period.

In a case where the first timing is included in the reading period of pixel signals of the first OB pixels, the timing generation circuit 105 may control the power supply voltage monitoring circuit 107 such that the power supply voltage monitoring circuit 107 stops detection of the power supply voltage. In other words, the timing generation circuit 105 may cause the power supply voltage monitoring circuit 107 to stop detection of the power supply voltage. Immediately after the first timing at which supply of the power supply voltage to the power supply voltage monitoring circuit 107 is started, the power supply voltage Vin held in the SH capacitor 124 is not stable due to switching of the detection switch 121 from off to on. Thus, detection of the power supply voltage may not be performed at the timing.

The timing generation circuit 105 may control the power supply voltage monitoring circuit 107 such that the power supply voltage monitoring circuit 107 starts detection of the power supply voltage in a reading period of pixel signals of the second OB pixels. The reading period is started at a second timing later than the first timing. It is highly likely that the power supply voltage Vin held in the SH capacitor 124 is stable in the second timing. Thus, the accuracy of detection of the power supply voltage by the power supply voltage monitor circuit 107 is improved.

The timing generation circuit 105 controls supply of the power supply voltage such that supply of the power supply voltage to the power supply voltage monitor circuit 107 is stopped at a third timing. That is, the timing generation circuit 105 causes the detection switch 121 to be turned off at the third timing. The third timing is later than the second timing.

An endoscope system according to each aspect of the present invention may not include at least one of the signal processing circuit 22, the signal output buffer 26, the operation panel 27, and the display 30. A solid-state imaging device according to each aspect of the present invention may not include at least one of the timing generation circuit 105, the column circuit 106, the output selecting circuit 108, and the signal output circuit 109.

In the first embodiment, the power supply voltage monitor circuit 107 detects the power supply voltage and outputs the first digital signal corresponding to the detected power supply voltage. The power supply voltage generated on the basis of the first digital signal is input to the power supply terminal 110. Thus, an appropriate power supply voltage is supplied to the solid-state imaging device 12, and thereby it is possible to suppress the fluctuation of the power supply voltage. That is, even when the voltage fluctuation due to an increase and a decrease of load current caused by the environment and the voltage fluctuation due to an operation mode of a sensor occur, it is possible to supply the highly accurate power supply voltage to the solid-state imaging device 12. Since fluctuation of the power supply voltage is suppressed, deterioration of image quality is suppressed.

The power supply voltage monitor circuit 107 is disposed within the solid-state imaging device 12. In a case where a circuit for detecting the power supply voltage is disposed independently of the solid-state imaging device 12 in the scope 10, the number of tips disposed in the scope 10 increases. Thus, wirings for electrically connecting the tips and the circuit board 11 increase. As a result, the mounting area of the circuit board 11 increases. The power supply voltage monitor circuit 107 is disposed within the solid-state imaging device 12, and thus it is possible to reduce the mounting area of the circuit board 11. That is, it is possible to miniaturize the scope 10.

The power supply voltage monitor circuit 107 is constituted by the SAR-ADC, and thus it is possible to miniaturize the power supply voltage monitor circuit 107. Thus, it is possible to miniaturize the solid-state imaging device 12. As a result, it is possible to reduce the mounting area of the circuit board 11.

The first and second digital signals are output from the signal output terminal 111 that is commonly used. Thus, it is possible to share a cable (the image transmission line 50) in transmission of the first and second digital signals. Since there is no need to prepare a cable for only the first digital signal, it is possible to thicken a cable (the power supply transmission line 40) for supplying the power supply voltage and reduce a resistance component of the cable. As a result, it is possible to supply the highly accurate power supply voltage to the solid-state imaging device 12 and deterioration of image quality is suppressed.

In a case where an analog signal representing a detection value of the power supply voltage detected in the solid-state imaging device 12 of the scope 10 is output to the processor 20, a cable for pixel signals and a cable for the detection value of the power supply voltage are necessary. In this case, the diameter of the entire cable bundling these cables becomes large. A cable is shared in transmission of the first and second digital signals, and thus it is possible to avoid the diameter of the entire cable from becoming large.

The first and second digital signals are output to the signal output terminal 111 by a common output circuit (the output selecting circuit 108 and the signal output circuit 109). Thus, it is possible to reduce the mounting area of the circuit board 11.

Generally, current consumption during a reading period of pixel signals is larger than that during a non-reading period of pixel signals. Thus, the power supply voltage in the reading period of pixel signals is lower than that in the non-reading period of pixel signals. Therefore, the power supply voltage monitor circuit 107 performs power supply voltage detection during the reading period of pixel signals, and thus it is possible to supply the highly accurate power supply voltage to the solid-state imaging device 12.

The power supply voltage monitoring circuit 107 detects the power supply voltage at least once each time imaging of one frame is performed. Thus, the power supply voltage monitoring circuit 107 is able to detect the power supply voltage that fluctuates due to the environment change in each frame. Also, the power supply voltage generation circuit 24 is able to set an appropriate power supply voltage on the basis of the detected power supply voltage.

Modified Example of First Embodiment

Figure 9:
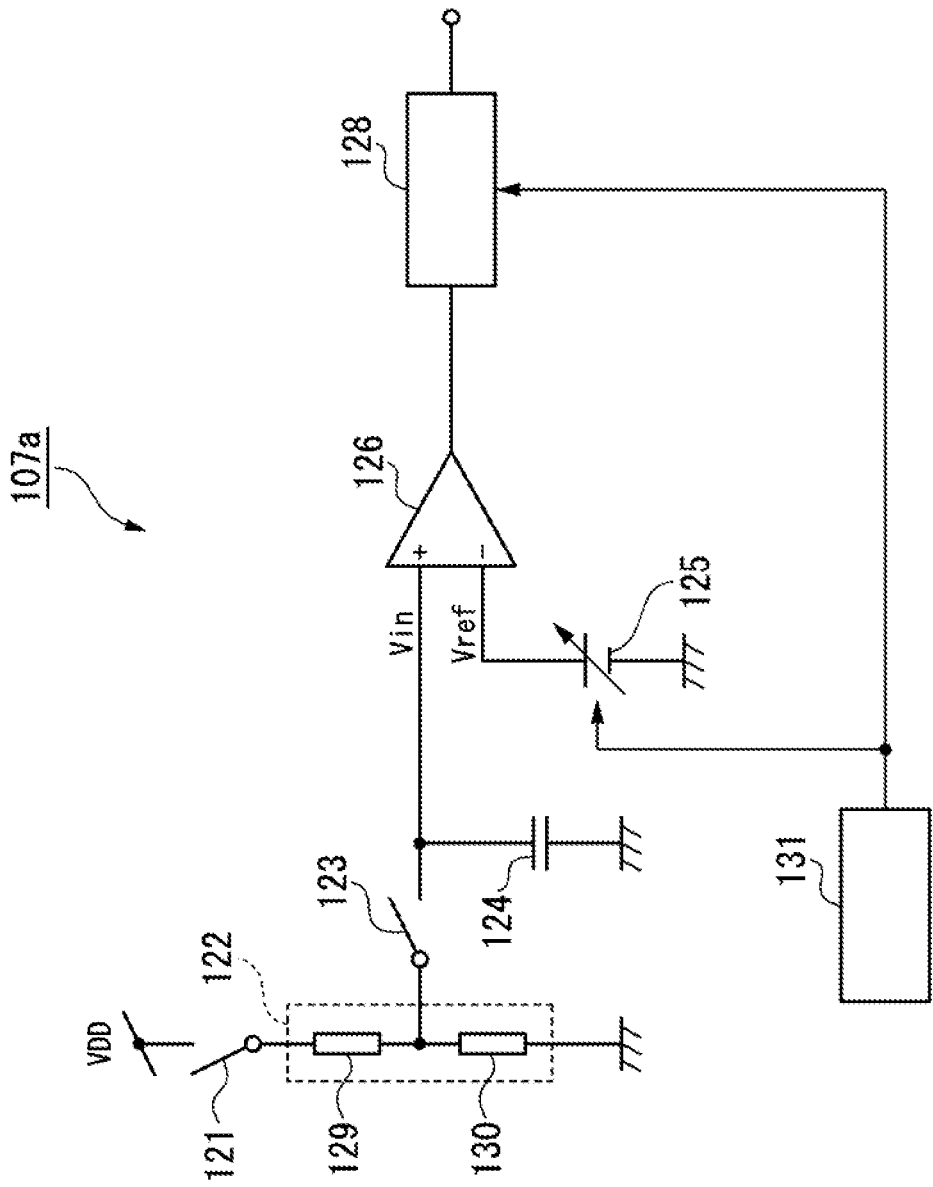
FIG. 9 is a circuit diagram showing a configuration of a power supply voltage monitoring circuit according to a modified example of the first embodiment of the present invention.

In the modified example of the first embodiment, the power supply voltage monitoring circuit 107 is constituted by a single slope analog-to-digital converter (SS-ADC). FIG. 9 shows a configuration of the power supply voltage monitoring circuit 107a constituted by the SS-ADC. Differences from the configuration shown in FIG. 3 will be described with respect to the configuration shown in FIG. 9.

The power supply voltage monitoring circuit 107a does not include the successive approximation logic 127 of the power supply voltage monitoring circuit 107 shown in FIG. 3. Also, the power supply voltage monitoring circuit 107a includes a counter 131. The counter 131 counts a predetermined clock signal and outputs a counted value to the reference voltage generation circuit 125 and the latch circuit 128. The reference voltage generation circuit 125 generates a reference voltage Vref according to the counted value. The reference voltage Vref monotonously increases or decreases. An example of power supply voltage detection in a case where the reference voltage Vref monotonously increases will be described below. The comparator 126 outputs a low level when the power supply voltage Vin is lower than the power supply voltage Vref. The comparator 126 outputs a high level when the power supply voltage Vin is higher than the power supply voltage Vref. When the high level is output from the comparator 126, the latch circuit 128 holds the counted value output from the counter 131. The counted value held in the latch circuit 128 constitutes the first digital signal.

In terms of points other than the above, the configuration shown in FIG. 9 is similar to the configuration shown in FIG. 3.

Figure 10:
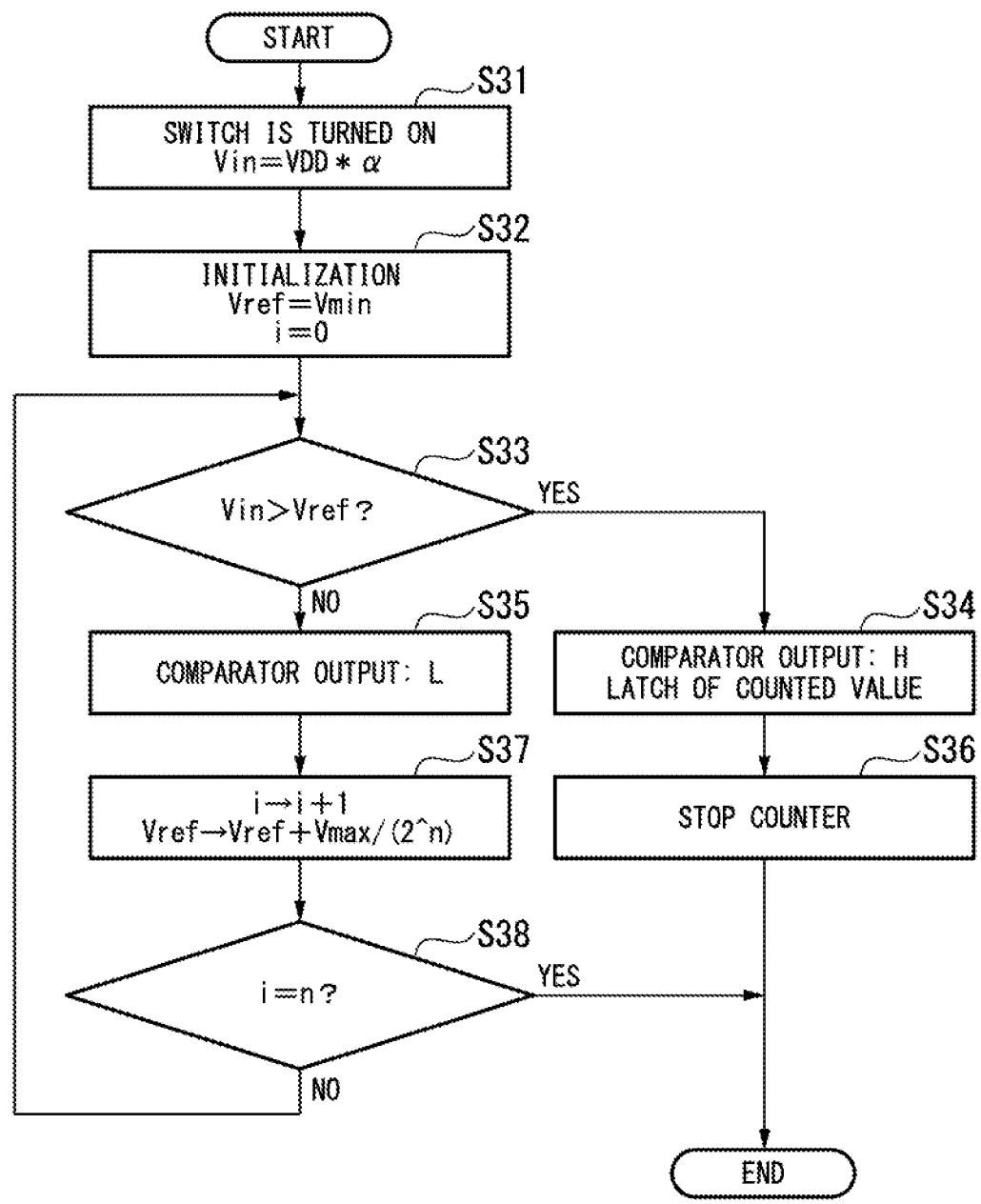
FIG. 10 is a flow chart showing a sequence of power supply voltage detection using the power supply voltage monitoring circuit according to the modified example of the first embodiment of the present invention.

FIG. 10 shows a sequence of power supply voltage detection using the power supply voltage monitoring circuit 107a. The number of bits of digital data constituting the first digital data output from the power supply voltage monitoring circuit 107a is n.

In step S31, the detection switch 121 and the SH switch 123 are turned on, and thus the power supply voltage Vin is input to the SH capacitor 124. Thereafter, the SH switch 123 is turned off, and thus the power supply voltage Vin is held in the SH capacitor 124.

In step S32, the counter 131 is initialized. Thus, the reference voltage Vref becomes Vmin. Vmin is the lowest voltage in the range of voltages that the reference voltage generation circuit 125 is capable of outputting. At this time, a counted value i is set to 0.

In step S33, the comparator 126 compares the power supply voltage Vin with the reference voltage Vref. When the power supply voltage Vin is higher than the reference voltage Vref the comparator 126 outputs a high level (step S34). When the power supply voltage Vin is lower than the reference voltage Vref the comparator 126 outputs a low level (step S35).

When the power supply voltage Vin is lower than the reference voltage Vref, the counted value i is increased by 1 in step S37. The reference voltage generation circuit 125 changes the reference voltage Vref on the basis of the counted value. The changed reference voltage Vref' is presented by following Expression (4).

$$Vref' = Vref + Vmax/(2^n) \qquad (4)$$

In step S38, when i is not equal to n in step S38, processes starting are similarly executed. In step S38 when i is equal to n, power supply voltage detection ends.

When the power supply voltage Vin is higher than the reference voltage Vref the latch circuit 128 holds the counted value output from the comparator 126 in step S34. Thereafter, the counter 131 is stopped in step S36.

After power supply voltage detection is started, the detection switch 121 is kept in a state of on. When power supply voltage detection ends, the detection switch 121 is turned off. Thus, supply of the power supply voltage to the power supply voltage monitoring circuit 107a is stopped.

Also in the modified example of the first embodiment, it is possible to supply the highly accurate power supply voltage to the solid-state imaging device 12 and reduce the mounting area of the circuit board 11.

Second Embodiment

Figure 11:
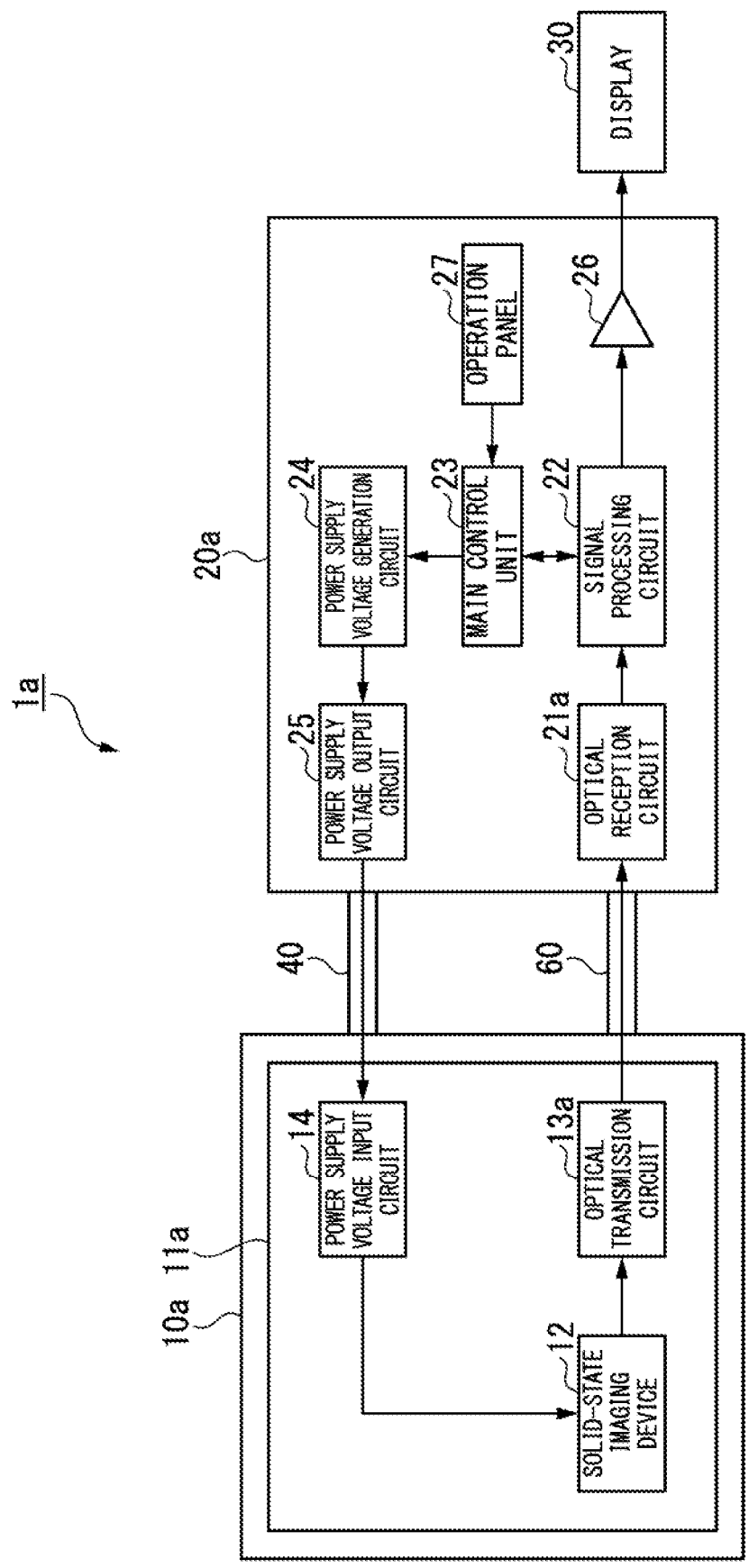
FIG. 11 is a block diagram showing a configuration of an electronic endoscope system according to a second embodiment of the present invention.

FIG. 11 shows a configuration of an electronic endoscope system 1a according to a second embodiment of the present invention. Differences from the configuration shown in FIG. 1 will be described with respect to the configuration shown in FIG. 11.

In the electronic endoscope system 1a, the scope shown in FIG. 1 is changed to a scope 10a and the processor 20 shown in FIG. 1 is changed to a processor 20a. In the electronic endoscope system 1a, the image transmission line 50 shown in FIG. 1 is changed to an optical fiber 60. In the scope 10a, the circuit board 11 shown in FIG. 1 is changed to a circuit board 11a. In the circuit board 11a, the signal output circuit 13 shown in FIG. 1 is changed to an optical transmission circuit 13a. In the processor 20a, the signal input circuit 21 shown in FIG. 1 is changed to an optical reception circuit 21a.

The first and second digital signals output from the signal output terminal 111 of the solid-state imaging device 12 are input to the optical transmission circuit 13a. The optical transmission circuit 13a convert the first and second digital signals into an optical signal and transmits the optical signal to the processor 20a. The optical signal output from the optical transmission circuit 13a is input to the optical fiber 60 and transmitted to the processor 20a by the optical fiber 60.

The optical signal transmitted by the optical transmission circuit 13a is received by the optical reception circuit 21a. The optical reception circuit 21a converts the optical signal into the first and second digital signals and output the first and second digital signals to the signal processing circuit 22.

In terms of points other than the above, the configuration shown in FIG. 11 is similar to the configuration shown in FIG. 1.

Also in the second embodiment, it is possible to supply the highly accurate power supply voltage to the solid-state imaging device 12 and reduce the mounting area of the circuit board 11a.

Third Embodiment

Figure 12:
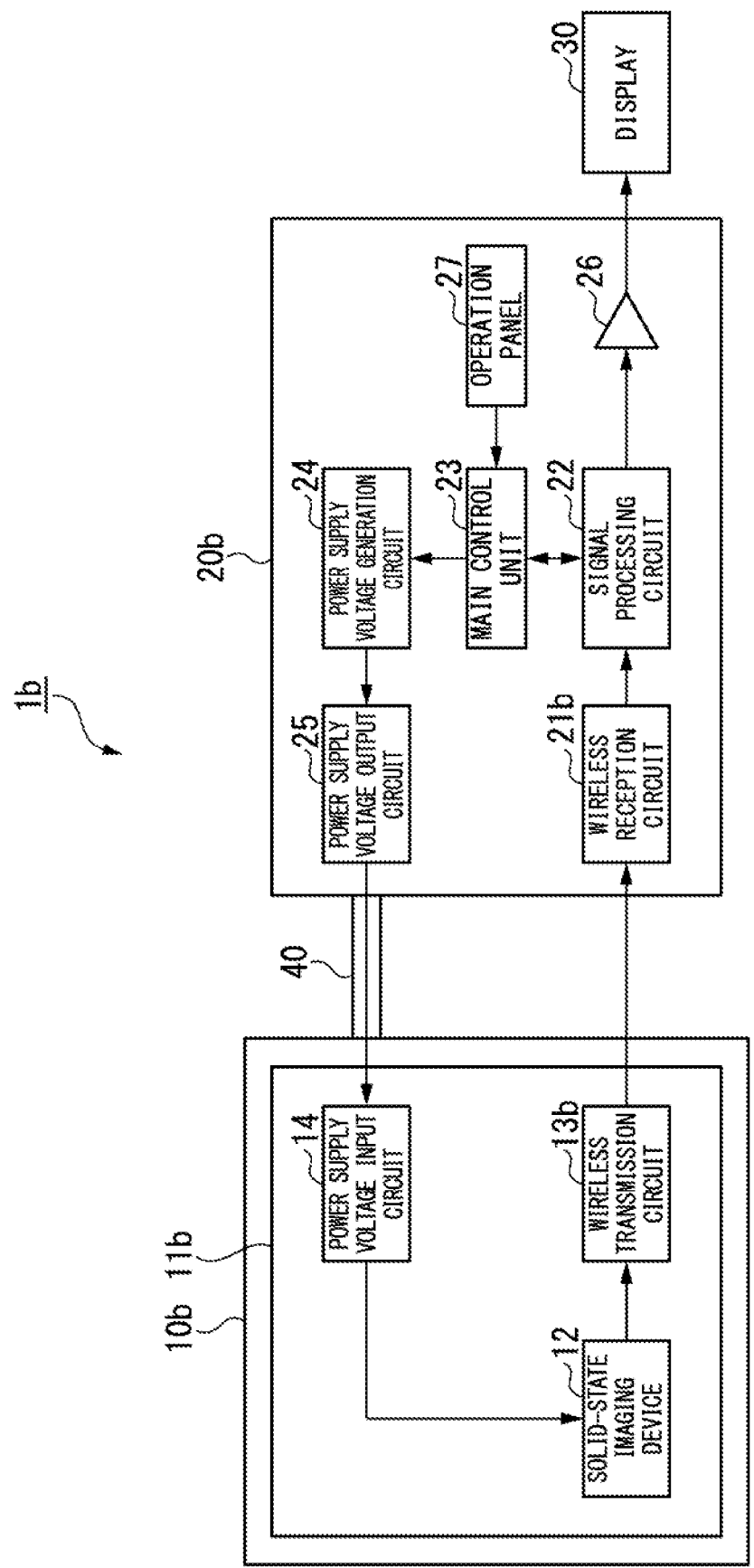
FIG. 12 is a block diagram showing a configuration of an electronic endoscope system according to a third embodiment of the present invention.

FIG. 12 shows a configuration of an electronic endoscope system 1b according to a third embodiment of the present invention. Differences from the configuration shown in FIG. 1 will be described with respect to the configuration shown in FIG. 12.

In the electronic endoscope system 1b, the scope shown in FIG. 1 is changed to a scope 10b and the processor 20 shown in FIG. 1 is changed to a processor 20b. The electronic endoscope system 1b does not include the image transmission line 50 shown in FIG. 1. In the scope 10b, the circuit board 11 shown in FIG. 1 is changed to a circuit board 11b. In the circuit board 11b, the signal output circuit 13 shown in FIG. 1 is changed to a wireless transmission circuit 13b. In the processor 20b, the signal input circuit 21 shown in FIG. 1 is changed to a wireless reception circuit 21b.

The first and second digital signals output from the signal output terminal 111 of the solid-state imaging device 12 are input to the wireless transmission circuit 13b. The wireless transmission circuit 13b wirelessly transmits the first and second digital signals to the processor 20b.

The first and second digital signals transmitted by the wireless transmission circuit 13b are received by the wireless reception circuit 21b. The wireless reception circuit 21b outputs the first and second digital signals that are wirelessly received to the signal processing circuit 22.

In terms of points other than the above, the configuration shown in FIG. 12 is similar to the configuration shown in FIG. 1.

Also in the third embodiment, it is possible to supply the highly accurate power supply voltage to the solid-state imaging device 12 and reduce the mounting area of the circuit board 11b.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A solid-state imaging device comprising:
   a plurality of pixels configured to generate pixel signals;
   a first control circuit configured to control timings at which the pixel signals are read from the plurality of pixels;
   a power supply terminal to which a power supply voltage is input;
   a power supply line that connects together the power supply terminal and the first control circuit;
   a detection circuit configured to detect the power supply voltage input to the power supply terminal after an imaging operation in the plurality of pixels is started, and output a first digital signal corresponding to the detected power supply voltage; and
   an output selecting circuit configured to selectively output the first digital signal output from the detection circuit and a second digital signal corresponding to the pixel signals to an output terminal.

2. The solid-state imaging device according to claim 1, wherein the power supply voltage generated on the basis of the first digital signal output from the output terminal is input to the power supply terminal.

3. The solid-state imaging device according to claim 1, wherein the detection circuit includes a successive approximation register analog-to-digital converter (SAR-ADC).

4. The solid-state imaging device according to claim 1, wherein the detection circuit is configured to detect the power supply voltage at least once each time imaging of one frame is performed, and output the first digital signal.

5. The solid-state imaging device according to claim 1, further comprising an AD conversion circuit configured to generate the second digital signal corresponding to the pixel signals read from the plurality of pixels.

6. The solid-state imaging device according to claim 5, further comprising an output circuit configured to output the first digital signal output from the output selecting circuit in a first output period to the output terminal, and output the second digital signal output from the output selecting circuit in a second period different from the first output period to the output terminal.

7. The solid-state imaging device according to claim 1, further comprising:
   an AD conversion circuit configured to generate the second digital signal corresponding to the pixel signals read from the plurality of pixels;
   an output circuit configured to output the second digital signal output from the output selecting circuit to the output terminal; and
   a second control circuit configured to control the detection circuit such that the detection circuit outputs the first digital signal in a period during which the output circuit stops output of the second digital signal.

8. The solid-state imaging device according to claim 7, wherein the first control circuit is configured to control timings at which the plurality of pixels generate the pixel signals,
   the first control circuit is configured to cause the plurality of pixels to generate the pixel signals in a first generation period, and thereafter cause the plurality of pixels to generate the pixel signals in a second generation period,
   the first control circuit is configured to read the pixel signals generated in the first generation period from the plurality of pixels, and thereafter read the pixel signals generated in the second generation period from the plurality of pixels,
   the second control circuit is configured to control the detection circuit such that the detection circuit outputs the first digital signal in a power supply signal output period,
   the power supply signal output period is included in a period after the output circuit ends output of the second digital signal corresponding to the pixel signals generated in the first generation period, and
   the power supply signal output period is included in a period before the output circuit starts output of the second digital signal corresponding to the pixel signals generated in the second generation period.

9. The solid-state imaging device according to claim 7,
wherein the first control circuit is configured to control timings at which the pixel signals are read from the plurality of pixels for each row in the arrangement of the plurality of pixels,
the second control circuit is configured to control the detection circuit such that the detection circuit detects the power supply voltage only in a reading period during which the pixel signals are read from the plurality of pixels,
the reading period does not include a horizontal blanking period,
the plurality of pixels include the pixel in a first row and the pixel in a second row different from the first row,
the horizontal blanking period is included in a period after reading of the pixel signal from the pixel in the first row is ended, and
the horizontal blanking period is included in a period before reading of the pixel signal from the pixel in the second row is started.

10. The solid-state imaging device according to claim 9,
wherein the plurality of pixels include a plurality of optical black pixels, and
the second control circuit is configured to control the detection circuit such that the detection circuit detects the power supply voltage only in a reading period of the pixel signals generated in the plurality of optical black pixels.

11. The solid-state imaging device according to claim 10,
wherein the plurality of optical black pixels include a first optical black pixel and a second optical black pixel,
the second control circuit is configured to control supply of the power supply voltage such that the power supply voltage is supplied to the detection circuit at a first timing,
the first timing is included in any one of a reading period of the pixel signal of the first optical black pixel and a period during which reading of all the pixel signals of the plurality of pixels is stopped,
the second control circuit is configured to control the detection circuit such that the detection circuit stops detection of the power supply voltage in a case where the first timing is included in the reading period of the pixel signal of the first optical black pixel,
the second control circuit is configured to control the detection circuit such that the detection circuit starts detection of the power supply voltage in a reading period of the pixel signal of the second optical black pixel,
the reading period of the pixel signal of the second optical black pixel is started at a second timing later than the first timing, and
the second control circuit is configured to control supply of the power supply voltage such that supply of the power supply voltage to the detection circuit is stopped at a third timing later than the second timing.

12. The solid-state imaging device according to claim 1, wherein the detection circuit is disposed within the solid-state imaging device.

13. An endoscope system comprising:
a circuit board; and
a control system,
wherein the circuit board includes
the solid-state imaging device according to claim 1,
a signal output circuit connected to the output terminal and configured to output the first digital signal and the second digital signal output from the output terminal to the control system, and
a power supply voltage input circuit,
the control system includes
a signal input circuit to which the first digital signal and the second digital signal output from the signal output circuit are input,
a power supply control circuit configured to determine the power supply voltage on the basis of the first digital signal input to the signal input circuit,
a power supply voltage generation circuit configured to generate the power supply voltage determined by the power supply control circuit, and
a power supply voltage output circuit configured to output the power supply voltage generated by the power supply voltage generation circuit to a power supply transmission line,
the power supply voltage output to the power supply transmission line is input to the power supply voltage input circuit, and
the power supply voltage input to the power supply voltage input circuit is input to the power supply terminal.

* * * * *